(12) United States Patent
Bürke et al.

(10) Patent No.: US 10,588,727 B2
(45) Date of Patent: Mar. 17, 2020

(54) DEVICE FOR PRODUCING DENTAL CERAMIC

(71) Applicant: Ivoclar Vivadent AG, Schaan (LI)

(72) Inventors: Harald Bürke, Frastanz (AT); Michael Spiegel, Lindau (DE); Oliver Voigt, Trübbach (CH)

(73) Assignee: Ivoclar Vivadent AG, Schaan (LI)

( * ) Notice: Subject to any disclaimer, the term of this patent is extended or adjusted under 35 U.S.C. 154(b) by 345 days.

(21) Appl. No.: 15/306,906

(22) PCT Filed: May 22, 2015

(86) PCT No.: PCT/EP2015/061446
§ 371 (c)(1),
(2) Date: Oct. 26, 2016

(87) PCT Pub. No.: WO2015/185381
PCT Pub. Date: Dec. 10, 2015

(65) Prior Publication Data
US 2017/0042647 A1    Feb. 16, 2017

(30) Foreign Application Priority Data
Jun. 6, 2014   (EP) .................................... 14171444

(51) Int. Cl.
*A61C 13/083*    (2006.01)
*A61C 13/00*    (2006.01)
(Continued)

(52) U.S. Cl.
CPC .............. *A61C 13/083* (2013.01); *A61C 5/77* (2017.02); *A61C 13/0004* (2013.01);
(Continued)

(58) Field of Classification Search
CPC .......... A61C 18/083; A61C 5/77; B29C 64/00
See application file for complete search history.

(56) References Cited

U.S. PATENT DOCUMENTS 5,768,134 A    6/1998 Swaelens et al.
6,691,764 B2   2/2004 Embert et al.
(Continued)

FOREIGN PATENT DOCUMENTS

JP    2005059477 A    3/2005
WO   20080103024 A1   8/2008

*Primary Examiner* — Jacob T Minskey
*Assistant Examiner* — Melody Tsui
(74) *Attorney, Agent, or Firm* — Ann M. Knab; Thad McMurray

(57) ABSTRACT

A device for producing dental ceramic, with a CAD/CAM device for preparing a compression molding cavity for producing the dental ceramic, wherein a CAD device thereof, on the basis of scan data, determines the shape of the dental ceramic to be produced, and wherein a CAM device thereof produces a positive model, on the basis of which the mold cavity is produced via a sacrificial mold (muffle). The CAM device also determines the distribution and the transfer between different ceramic types, i.e. types of ceramics that differ at least in respect of one parameter in terms of material, appearance, strength or the like, wherein the CAM device for adjusting the distribution and the transfer determines the position and the dimensions of a feed channel between a muffle rod and the compression molding cavity for producing the dental ceramic according to at least one of these parameters.

24 Claims, 4 Drawing Sheets

(51) Int. Cl.
    *A61C 13/08*     (2006.01)
    *B33Y 80/00*     (2015.01)
    *A61C 5/77*     (2017.01)
    *B28B 7/00*     (2006.01)
    *B29K 91/00*     (2006.01)
    *B29L 31/00*     (2006.01)

(52) U.S. Cl.
    CPC ...... *A61C 13/0019* (2013.01); *A61C 13/0022* (2013.01); *A61C 13/081* (2013.01); *A61C 13/082* (2013.01); *B28B 7/0097* (2013.01); *B33Y 80/00* (2014.12); *A61C 2201/002* (2013.01); *B29K 2091/00* (2013.01); *B29L 2031/753* (2013.01); *B29L 2031/757* (2013.01)

(56) References Cited

U.S. PATENT DOCUMENTS

| | | |
|---|---|---|
| 7,691,497 B1 | 4/2010 | Brodkin et al. |
| 2008/0142183 A1* | 6/2008 | Marshall ................. B22C 7/02 164/36 |
| 2008/0153069 A1 | 6/2008 | Holzner et al. |

* cited by examiner

DEVICE FOR PRODUCING DENTAL CERAMIC

CROSS-REFERENCE TO RELATED APPLICATIONS

This application is a National Stage application of International patent application PCT/EP2015/061446 filed on May 22, 2015, which claims priority to European patent application No. 14171444.4 filed on Jun. 6, 2014, the disclosures of which are incorporated herein by reference in their entirety.

The invention relates to a device for producing dental ceramic according to the preamble of claim 1.

It has been known for a relatively long time to produce a dental restoration using three-dimensional scan data from the mouth of a patient. An example of this is the method known from WO 95/28688 A1 according to which a positive model is produced by means of rapid prototyping which can serve as a base for molding a negative mold or sacrificial mold.

It has also been known for long to merge ceramic materials, which differ from one another with respect to at least one parameter, appropriately, and to use them together for providing the dental restoration. In this respect, according to EP 0 781 530 A2 a tetragonally stabilized zirconium oxide ceramic is provided as a reinforcement material which is surrounded by a ceramic veneer. The ceramic veneer can also be varicolored and can be fired onto or pressed onto the reinforcement ceramic (see e.g. claim 10).

A further example of different dental ceramic materials, also with filling materials, which can also be combined with one another, can be taken from U.S. Pat. No. 6,345,984 B2.

It has also been suggested already to produce two matching molds of individual components for a dental restoration in a CAD/CAM process and to connect them with one another in a joining step. However, this solution is relatively complex and leads to a certain uncertainty with regard to the height level, depending on the thickness of the adhesive layer between the individual components which has been applied manually.

Furthermore, it has already been suggested to press together two differently colored ceramic masses and to attach a bulge at the feed channel at a suitable position to reduce the share of one of the ceramic masses in the finished dental restoration in this way. However, this solution has not become established in practice either; in most cases, test pressings are required for determining the transition such that this method is not justifiable with regard to the effort.

Contrary to this, the invention is based on the task of providing a device for producing dental ceramic according to the preamble of claim 1, which is easier to handle and enables the reliable production of a dental ceramic from at least two different ceramic types.

This task is inventively solved by claim 1. Advantageous developments may be taken from the subclaims.

According to the invention, it is particularly favorable that the CAM device performs an automatic determination of the distribution and the transition between the different ceramic types. This is done by automatically adjusting the position of the feed channel, the dimensions of the feed channel, the relative height of the feed channel with respect to the compression molding cavity on the one hand, but also the muffle rod which corresponds to the press channel on the other hand by the CAM device when the positive model is produced.

This is done by automatically adjusting the position of the feed channel which corresponds to the press channel, the dimensions of the feed channel, the relative height of the feed channel with respect to the muffle rod on the one hand, but also the compression molding cavity on the other hand by the CAM device when the positive model is produced.

For this purpose, a blank with a known distribution of ceramic types which differ from one another at least with regard to one parameter is initially used. According to the invention, the dental restoration is to also consist of at least two ceramic types, but the distribution and the transition must not correspond to the distribution and the transition of the ceramic blank. For this purpose, the feed channel is used in an inventively rather surprisingly easy manner which is provided in line with the objective by the CAM device. For instance, a wedge-shaped configuration of the feed channel, as viewed in cross section, results in a larger flow resistance of the ceramic type adjacent to the tip of the wedge such that the transition and the distribution in the dental restoration are shifted more strongly to the other type.

This also provides the possibility of using two very different ceramic types which differ from one another for instance with respect to one parameter by 80%, but of adjusting a difference of only for instance 40% with the ceramic types of the dental ceramic by means of a smaller height of the feed channel.

As the CAM device produces the feed channel together with the compression molding cavity by means of rapid prototyping or in any other suitable manner it is easily possible to ensure a corresponding relative position in advance and thus without any errors, and thus to automatically preset the distribution and the transition, too—without the need of manual post-processing.

It is also easily possible for instance to provide a lateral constriction in the feed channel which can, for instance, be configured in a bulged manner and to realize a spreading of the distribution and the transition at the dental ceramic compared to the blank, in this way.

Typically, an inventive feed channel comprises a height which is substantially larger than its thickness. Height means the direction of the change sequence of the ceramic types, both in case of the pressed blank and the dental restoration. Typically, upper areas of the pressed blank are supplied to upper areas of the dental ceramic via the feed channel accordingly, and vice versa, lower areas of the dental ceramic are supplied to lower areas of the pressed blank.

In an advantageous embodiment of the inventive device it is provided that several dental restorations together with corresponding feed channels extend away from the press channel or muffle rod. The feed channels can be connected to one another via a shared feed base and can be produced together by means of rapid prototyping—or also by milling. Alternatively, every feed channel together with the associated positive model of the dental restoration can also be produced separately, wherein in this case the feed channels are attached to the muffle rod with their inflow ends, which muffle rod offers a corresponding height stop at the same time in this case.

The dental restorations extend preferably circularly around the muffle rod or the corresponding press channel and keep an edge distance towards the outer wall of the muffle which should not fall below 10 mm. At the same time, the dental restorations also keep a distance of for instance 3 or 4 mm to one another. The circular space is defined by the CAM section of the CAD/CAM device as a virtual space within which the compression molding cavity and the feed channel must extend within the muffle and wherein the virtual ring space is marked visually within the muffle, optionally in case of possible user intervention, with regard to the position of the compression molding cavity for the dental ceramic.

After the arrangement of dental restorations and feed channels has been produced by means of rapid prototyping, this arrangement is attached to the muffle rod appropriately and secured thereat. In a way known per se a silicone ring is pushed onto a muffle base, and then the unit consisting of muffle base, muffle rod and pre-fabricated positive models including the feed channels is cast by means of a suitable curable mass such as a phosphate-bonded investment material; for lower press temperatures, a plaster compound is also suitable.

After the mass has cured, the silicone ring is removed and the muffle base is pulled out together with the muffle rod. In this connection, the arrangement produced by rapid prototyping is separated from the muffle rod and stays in the muffle.

It consists of a mass which can be removed without leaving residues. For this purpose, the muffle is heated to a suitable temperature at which the material of the positive models melts or even vaporizes, or burns without leaving residues.

After this step the compression molding cavities and the press channel stay at the position at which the muffle rod extended before. Between them the inventively configured feed channels are provided.

Typically, the muffle is turned around now as the press furnaces used for dental technology comprise a plunger which moves from top to bottom. After a multi-ceramic blank has been inserted, a distance disk or a distance cylinder or both, for instance made of aluminum oxide or of a phosphate-bonded investment material, are inserted, and subsequently the pre-heated muffle is inserted into the press furnace where it is heated to the press temperature.

Due to the heating process the ceramic becomes viscous and due to the pressure applied by the plunger it flows through the feed channels into the compression molding cavities.

The temperatures in question amount to between 850° C. in case of lithium disilicate ceramics and 1200° C. in case of, for instance, leucite glass ceramics or oxide ceramics.

When the arrangement of feed channels and positive models is produced integrally, the optionally desired height offset according to the invention can be realized both on the output side but preferably also on the input side of the feed channel and optionally also on both sides. Furthermore, there are ample possibilities in terms of the selection of the shape of the feed channel.

According to the invention, the particular task of the CAM device is to select the shape of the feed channel such that an aesthetically particularly attractive result is provided, but also a result which corresponds to the load requirements of the dental restoration. With ceramic types which differ from one another in terms of the material the CAM device ensures that the material used as a reinforcement element, such as oxide ceramics, is supplied to the dental restoration sufficiently, that is to say to the compression molding cavity for the dental restoration.

For this purpose the cross-sectional flow area of the feed channel at the end face of the press channel or adjacent to this area is sufficiently broad. Typically, the darker and/or harder ceramic material is supplied at the end of the press channel, that is to say, in case of a muffle arrangement in which the muffle base is at the bottom, from the top, wherein the compression molding cavity is oriented such that the incisal or occlusal area is at the bottom in this case.

Here, this view is taken as a general basis, wherein it is to be understood that the muffle is turned by 180° in the pressing process; however, this position is not explained any further at this point.

Then, the pressed blank—and thus also the finished dental ceramic—comprises the softer and/or lighter ceramic material at the bottom, and the vertical relative position between the feed channel and the compression molding cavity influences the flow therein, and thus the distribution of the ceramic types in the dental restoration. Due to the frictional effects between the upper and the lower end of the feed channel the flow of ceramic material is decelerated thereat respectively such that the flow front of ceramic material is typically bulged, that is to say bellied at the center.

To meet this occurrence a central constriction of the feed channel can also be provided.

In a further advantageous embodiment one or more load-relief projections are provided which extend along the longitudinal side of the feed channel transversely to the direction of flow and into which the dental ceramic enters before it continues to flow. In this way, flow equalization can be produced.

In a further preferred embodiment it is provided to attach the feed channel as an extension of the incisal or occlusal extension of the center of gravity. For this purpose, the mesiobuccal cusp lends itself with molars, wherein in that case the feed channel extends preferably substantially mesially therefrom, however, preferably slightly obliquely, quasi as an extension of the buccal outer surface of the dental restoration.

With anterior teeth, the feed channel is oriented preferably along the labial surface in the same manner, that is to say as an extension of the tooth edge, however, slightly angled in the lingual direction relative to it.

This orientation optimizes the inflow of the front of dental ceramic material into the compression molding cavity of the dental ceramic.

In a further embodiment it can be advantageous particularly with molars to attach the feed channel in a straight extension of the central fissure in order to ensure a particularly symmetrical distribution of the different ceramic types.

If necessary, the gradients of the transition or the distribution of the ceramic types can also be changed using overflow spaces. They extend preferably at the muffle rod, wherein this intervention has an influence on all objects of the press muffle, or on the feed channel itself. In the latter case, the intervention has an influence on the individual restoration.

Then, at the beginning of the pressing process, the dental material flows directly into the overflow space located thereat, and is provided in the restoration at a correspondingly low percentage share.

It is particularly favorable if a circumferential bead is attached at the feed channel which can consist of wax, said bead ending flush with the muffle rod, after the feeder has been inserted into the provided groove at the muffle rod. In this way, attachment using wax is facilitated substantially and possible damage to the feeder profile is prevented effectively.

Further advantages; details and features may be taken from the following description of several exemplary embodiments of the invention in conjunction with the drawings, in which.

Figure 1:
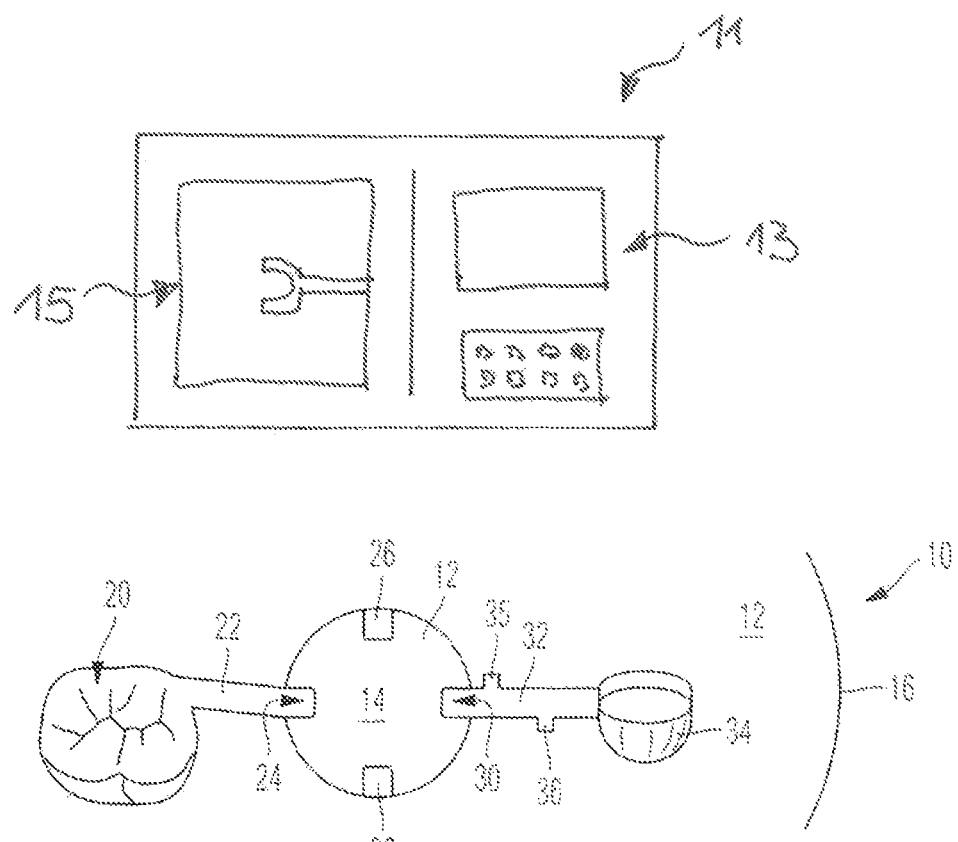
FIG. 1 shows a schematic view of a parts of a CAD/CAM device for producing dental ceramic, which illustrates a CAM section, a CAD section, a muffle rod (12), two feed channels and two mold cavities for the production of dental ceramics, in the top view towards the muffle rod (12)

The device for producing dental ceramic 10 illustrated in FIG. 1 in a very small part uses—as illustrated above—a CAD/CAM device 11 with CAD section 13 and CAM section 15 to provide a positive model to be embedded. Said positive model is illustrated in FIG. 1. A muffle rod 12 extends from a muffle base which is below the drawing plane and ends at an end face 14. At the same time the muffle base forms the bottom side of a muffle whose muffle edge 16 is also illustrated schematically in FIG. 1.

In the embodiment of FIG. 1 feed channels and compression molding cavities are produced as positive models by CAD/CAM, namely with a rapid prototyping method suitable for this purpose. Among them is a positive model 20 of a molar whose cervical side is arranged adjacent to the end face 18, approximately at the same level. The positive model 20 forms the corresponding compression molding cavity for the dental ceramic after the muffle has cured and the rapid prototyping material consisting of a polyacrylic material has been burnt out.

It is produced integrally with the associated feed channel 22 which is configured in a particular manner. It is accommodated in a groove 24 of the muffle rod 12 and is produced by the rapid prototyping shaping step in a height level which is more apparent from FIG. 2 and which corresponds to the desired distribution of the ceramic types. For this purpose, a ceramic blank is used in the later pressing process which consists of several ceramic types with a corresponding transition, for instance of two different ceramic materials or ceramics with different colors. By way of example, the varied distribution of colors is addressed here.

Figure 2:
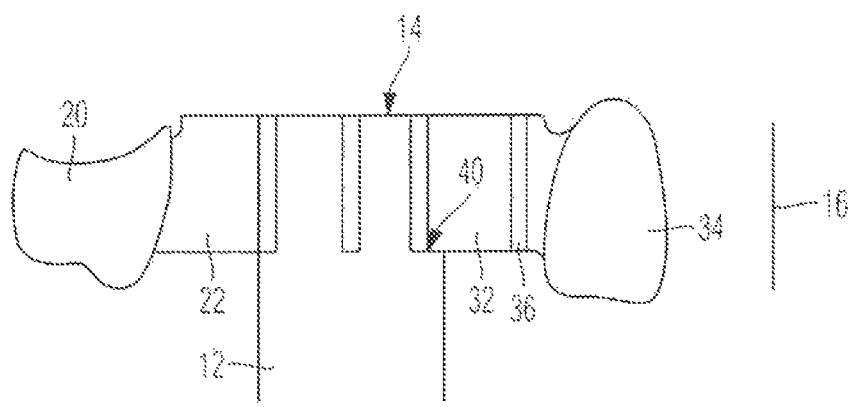
FIG. 2 shows a side view of the embodiment of FIG. 1.

The height level apparent from FIG. 2 which is preset by the CAM device after user selection has an influence on the distribution of colors, in particular on the final values. Moreover, by correspondingly configuring the feed channel 22 the transition can be influenced, and it is referred to FIG. 4a to FIG. 4e in this context, by way of example. Besides the groove 24, the muffle rod 12 comprises three further grooves 26 to 30. They are intended for the accommodation of further feed channels, wherein in the exemplary case the groove 30 is provided with the feed channel 32. A positive model 34 is integrally connected with the feed channel 32 to form a mold cavity for an anterior tooth. Typically, anterior teeth are aesthetically more important in terms of the exact color structure, both when it comes to translucency and to the adaptation to the neighboring teeth.

The feed channel 32 comprises pressure-reduction spaces or load-relief projections 35 and 36 which serve to equalize the flow. They can also be selected to be larger by the CAM device in order to adjust the volume of the positive model 34 with the feed channel 32 to the volume of the positive model 20 with the feed channel 22 and to ensure a simultaneous completion in this way. The CAM section of the CAD/CAM device, depending on the volume of the compression molding cavity 34, determines the thickness of the feed channel and when the volume of the compression molding cavity 34 is below a predetermined threshold value, pressure-reduction spaces 35 and 36 are included in the feed channel, which relax the ceramic during the pressing process which advances and is under isostatic pressure during the pressing process.

It is preferred that the flow front of the softened dental ceramic simultaneously fills the compression molding cavities.

It is apparent from FIG. 2 that the occlusal or incisal sides of the teeth extend downwards, which means that, in the exemplary case, the lighter ceramic types of the blank also need to be directed downwards.

By vertically shifting by means of rapid prototyping the colorfulness or brightness of the dental restorations can be influenced; in the exemplary case it is provided that the feed channels 22 and 32 are seated via stops 40 at a vertically preset position at the muffle rod 12 in the grooves 24 or 30, while in a modified embodiment it is provided to vary also the relative position between the feed channel 22 and 32 and the muffle rod 12.

It is apparent that the distance between the compression molding cavity 34 and the muffle edge 16 is predetermined; preferably, this distance amounts to at least 10 mm, even if a smaller distance is illustrated here for graphical reasons.

Nowadays, modern press furnaces for pressing dental ceramic parts typically comprise a so-called floor heating. This heating heats the region below the muffle and adds to a ring heating which surrounds the muffle in the shape of a ring and which primarily serves to heat the interior of the furnace.

However, in many cases press furnaces are used which get along without a floor heating. In this case, the ring heating is the only heating. As a result, the muffle is heated from the outside to the inside. Because of this cone-shaped isothermal passages arise, just like passage 44 which is illustrated in FIG. 3 by way of example.

Due to the flexibility of rapid prototyping, for a furnace of this kind an optimization in the configuration of the feed channel 32 can be performed such that both the positive model 34 and the feed channel 32 extend in an isothermal passage 44. As in this solution the flow path in the lower area 46 of the feed channel 32 is longer than in the upper area 48, compensation by means of a corresponding shape of the feed channel takes place in an inventively particularly preferable manner, for instance the shape according to FIG. 4a. The flow resistance will then be lower in the area 46 than in the area 48 such that the extension of the flow path is compensated for in this respect.

Figure 3:
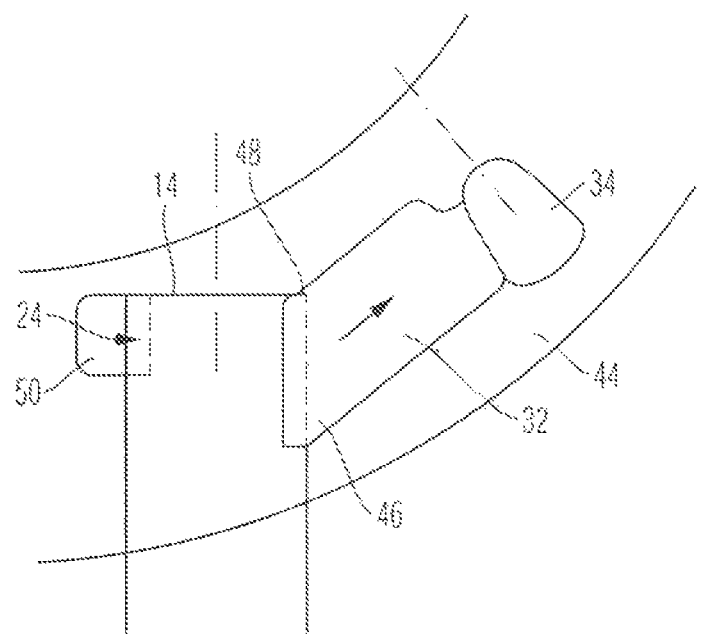
FIG. 3 shows a modified embodiment, in the view of FIG. 2.

In the exemplary embodiment illustrated in FIG. 3 in the upper area, that is to say adjacent to the end face 14, an overflow space 50 is additionally configured in the groove 24, said overflow space also compensating for the tendency of the softening dental ceramic material to pass through the area 48 rapidly.

The feed channels 22 and 32 are typically in the shape of a thin wall or small plate-like section having a length of at least 3 mm. The feed channels 22 and 32 extend transversely to the compression molding cavity for the dental ceramic. Different feed channel shapes are apparent in the cross section from FIGS. 4a to 4e. For instance, the feed channel 32 according to FIG. 4a can be narrower in area 48 and broader in area 46. According to FIG. 4a the feed channel 32 comprises rounded edges on all sides such that the flow resistances are comparatively low thereat The CAM device includes a feed channel library by means of which, optionally by user intervention, the distribution and the transition between the different ceramic types in the dental ceramic can be determined based on predetermined distribution patterns or transition patterns.

Figure 4:
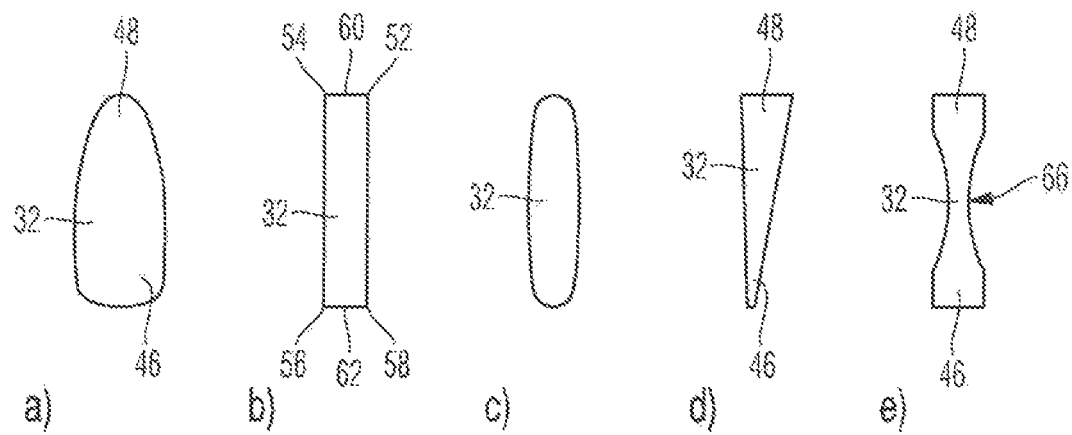
FIG. 4a-4e show cross-sectional views of feed channels for the inventive device for producing dental ceramic.

According to FIG. 4b a rectangular cross-sectional flow area of the flow channel 32 is selected. Here, the main braking effects occur along the edges 52, 54, 56 and 58, but also along the upper side 60 and along the bottom side 62. With this shape the flow front is centrally bulged and lags behind considerably in the edges 52 to 58. As a consequence, in an embodiment of this type the central area is filled with dental ceramic material initially such that color spreading occurs in this respect.

In the cross-sectional profile of the feed channel according to FIG. 4c the edge effects are smaller by way of contrast such that less color spreading occurs.

In the wedge-shaped cross-sectional flow area according to FIG. 4d the darker upper area 48 is emphasized and accordingly there is a color shift towards this area, as the flow resistance in area 46 is considerably higher.

The constricted shape according to FIG. 4e compensates for the color spreading described in conjunction with FIG. 4b as the flow resistance in the central area 66 is kept larger consciously thereat.

These shapes can be produced in any desired manner by rapid prototyping integrally with the positive model 32.

Figure 5:
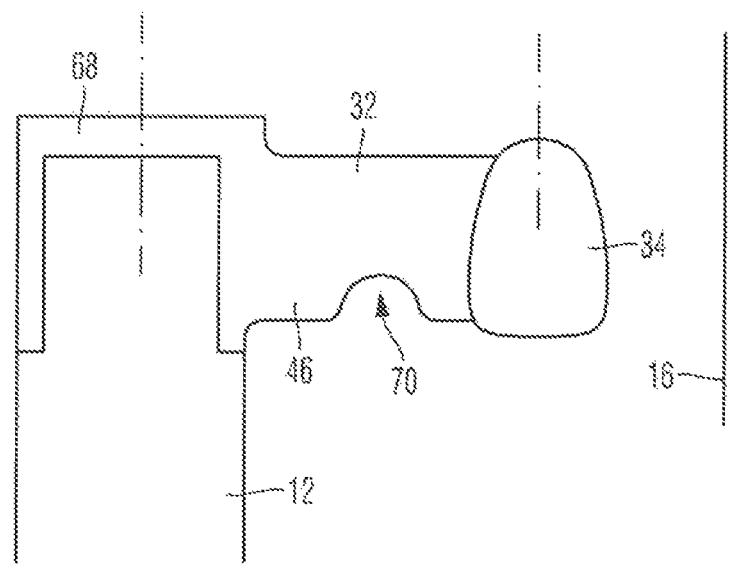
FIG. 5 shows a side view of a further mold produced by rapid prototyping for a press channel, a feed channel and a compression molding cavity.

According to FIG. 5 it is provided to produce feed channels, of which one feed channel 32 is illustrated, and positive models, of which one positive model 34 is illustrated, integrally. For this purpose, a feed channel base 68 is provided which extends cap-shaped across the muffle rod 12. In this exemplary embodiment the muffle rod 12 can be detached particularly easily from the cured muffle.

In this exemplary embodiment the feed channel 32 additionally comprises a constriction 70 in the incisal area 46 which leads to the color distribution shifting to darker colors.

Figure 6:
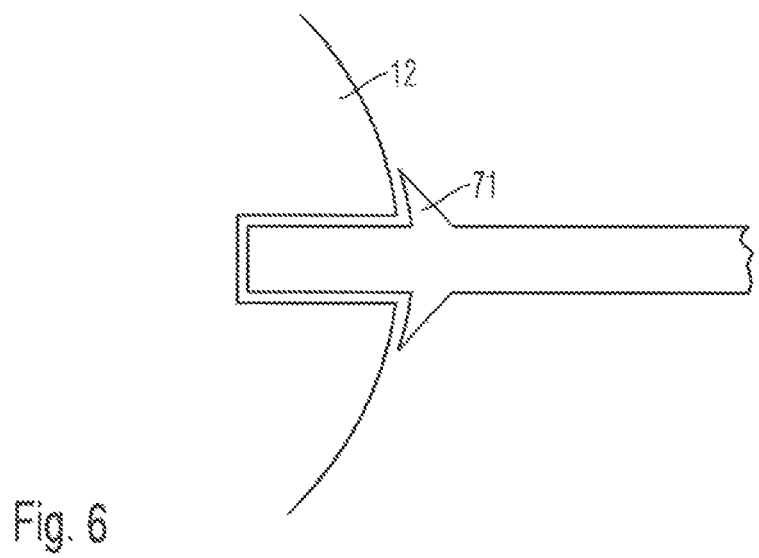
FIG. 6 shows a plan view of a feed channel made of wax with a circumferential bead as an accumulation aid.

According to FIG. 6 a feed channel is fabricated in wax. In this connection, it is advantageous if a circumferential bead 71 is attached which ends flush with the muffle rod 12 after the feeder has been inserted into the provided groove 24. In this way, accumulation is facilitated considerably. Possible damage to the feed profile can be prevented effectively.

Figure 7:
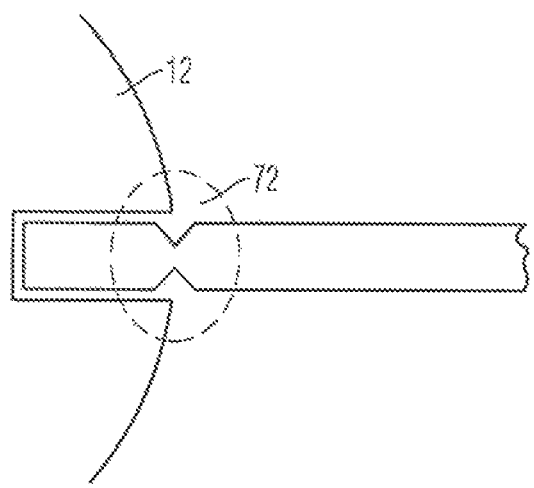
FIG. 7 shows a plan view of a feed channel made of polymeric material with a predetermined breaking point.

According to FIG. 7 the feed channel is made of a polymeric material, for instance polyacrylics. In this connection, it is favorable to attach a predetermined breaking point at the transition point between the attachment groove 24 and the free feed channel such that the muffle base with the muffle rod can be detached easily by means of a rotating movement after the investment material has cured.

The invention claimed is:

1. A production device for producing dental ceramic comprising
a CAD/CAM device configured to provide a compression molding cavity for producing the dental ceramic,
wherein the CAD section of the CAD/CAM device determines a shape of the dental ceramic to be produced, and
wherein the CAM section of the CAD/CAM device produces a positive model for producing a mold cavity,
wherein the CAM section of the CAD/CAM device determines the distribution and the transition between different types of ceramic materials that differ at least in respect of one parameter,
wherein the CAM section of the CAD/CAM device determines the position and the dimensions of a feed channel (22, 32) between a muffle rod (12) and the compression molding cavity (34) for producing the dental ceramic based the at least one parameter of the ceramic materials.

2. The production device as claimed in claim 1,
wherein by the CAM section of the CAD/CAM device the feed channel (22, 32) in the form of a thin wall or plate-like section having a length of at least 3 mm can be produced,
said feed channel extending from a muffle rod (12), transversely to the compression molding cavity (34) for the dental ceramic,
wherein the muffle rod can be used as a press channel in a pressing process.

3. The production device as claimed in claim 1,
wherein by the CAM section of the CAD/CAM device the tilt angle and/or the height level between the compression molding cavity (34) for the dental ceramic and the feed channel (22, 32) can be determined, both in the vertical and in the horizontal direction.

4. The production device as claimed in claim 1,
wherein by the CAM section of the CAD/CAM device both the compression molding cavity (34) and the feed channel (22, 32) can be produced, integrally and by additive manufacturing, from wax or from a plastic material by means of rapid prototyping.

5. The production device as claimed in claim 1,
wherein by the production device (10) vertical position of the feed channel (22, 34) with respect to the compression molding cavity can be determined (34) and can vary to influence the color and brightness of the dental ceramic.

6. The production device as claimed in claim 1,
wherein by the CAM section of the CAD/CAM device the orientation of the compression molding cavity (34) can be selected such that the incisal/occlusal side of the dental ceramic of the compression molding cavity (34) is directed towards the muffle base and the basal side towards the end of the muffle rod (12).

7. The production device as claimed in claim 1,
wherein by the CAM section of the CAD/CAM device a virtual space can be defined within which the compression molding cavity (34) and the feed channel (22, 32) must extend within the muffle and
wherein the virtual ring space is marked visually within the muffle, optionally in case of possible user intervention, with regard to the position of the compression molding cavity (34) for the dental ceramic.

8. The production device as claimed in claim 1,
wherein by the CAM section of the CAD/CAM device the longitudinal axes of the compression molding cavity (34) for the production of the dental ceramic and of the plate-shaped feed channel (22, 32) can be aligned parallel to one another.

9. The production device as claimed in claim 1,
wherein the vestibular (labial or buccal) sides of the feed channel (22, 32) and the compression molding cavity (34) are aligned substantially flush with one another, and
wherein the horizontal axis of the feed channel (22, 32) passes through the compression molding cavity (34) and the horizontal axis but is deflected with respect to a longitudinal axis in the vestibular direction.

10. The production device as claimed in claim 1,
wherein by the CAM section of the CAD/CAM device the connection point between the feed channel (22, 32) and the compression molding cavity (34) can be selected for the production of the dental ceramic at a proximal peripheral region of the compression molding cavity (34).

11. The production device as claimed in claim 1, wherein by the CAM section of the CAD/CAM device the thickness of the feed channel (22, 32) depending on the volume of the compression molding cavity (34) determined by calculation can be determined, and in case of volumes below a predetermined threshold value pressure-reduction spaces can be formed at the feed channels (22, 32) and/or at the press channel corresponding to the muffle rod (12), said pressure-reduction spaces relaxing the ceramic which advances and is under isostatic pressure during the pressing process.

12. The production device as claimed in claim 1, wherein the compression molding cavity (34) comprises a rod for the formation of a stump for the dental ceramic, and wherein the longitudinal axis of the feed channel (22, 32) is oriented with respect to the compression molding cavity (34) such that it intersects the compression molding cavity (34) outside of the rod and/or that the longitudinal axis of the feed channel is configured asymmetrically with regard to an axis of the rod.

13. The production device as claimed in claim 1, wherein the height of a feed channel (22, 32) corresponds to the a height of a molded part which is accommodated in a muffle for the formation of a multi-colored dental ceramic, or is at most 20% smaller than a height of the a blank.

14. The production device as claimed in claim 1, wherein a muffle rod (12) is provided for accommodating plate-shaped feed channels (22, 32), which comprises at least two slots for the accommodation thereof, a vertical extension of which forms a stop for a vertical orientation of the feed channels (22, 32).

15. The production device as claimed in claim 14, wherein a muffle rod (12) for accommodating and mounting the feed channels (22, 32) for the compression molding cavities (34) for the production of the dental restoration is provided, and wherein the feed channels (22, 32) are connected with each other by means of a shared hood which is intended for the accommodation at the muffle rod (12).

16. The production device as claimed in claim 1, wherein by the CAM section of the CAD/CAM device differences in viscosity between the ceramic materials can be balanced by means of pressure-reduction spaces and/or flow obstructions at least partially, said pressure-reduction spaces and/or flow obstructions being arranged at the press channel, at one of the feed channels (22, 32) or at both or all of them.

17. The production device as claimed in claim 1, wherein the CAM section of the CAD/CAM device comprises a feed channel library by means of which, optionally by user intervention, the distribution and the transition between the different ceramic materials in the dental ceramic can be determined based on predetermined distribution patterns or transition patterns.

18. The production device as claimed in claim 1, wherein a circumferential bead (71) is attached to the feed channel (32), said bead ending flush with the muffle rod (12), after the feed channel (32) has been inserted into a provided groove (30) at the muffle rod (12).

19. The production device as claimed in claim 1, wherein the feed channel (22) is made of a polymeric material and comprises a predetermined breaking point (72) at a transition point from an attachment groove (24) to a free feed channel (22).

20. The production device as claimed in claim 1, wherein the mold cavity is provided using a muffle.

21. The production device as claimed in claim 1, wherein the at least one parameter of the different types of ceramic materials comprise composition, appearance, and/or strength.

22. The production device as claimed in claim 4, wherein the plastic material comprises polyacrylics.

23. The production device as claimed in claim 14, wherein the muffle rod (12) comprises at least four slots for accommodating plate-shaped feed channels.

24. The production device as claimed in claim 14, wherein the polymeric material comprises polyacrylics.

* * * * *